(12) United States Patent
Malik et al.

(10) Patent No.: US 6,967,259 B2
(45) Date of Patent: Nov. 22, 2005

(54) PROCESS FOR THE PREPARATION OF CITALOPRAM INTERMEDIATE

(75) Inventors: Aslam A. Malik, Cameron Park, CA (US); Hasan Palandoken, Woodland, CA (US); Joy A. Stringer, West Sacramento, CA (US); DerShing Huang, Folsom, CA (US); Antonio Romero, Irvine, CA (US); Olivier Dapremont, Folsom, CA (US)

(73) Assignee: Pharmachem Technologies Limited (GB)

( * ) Notice: Subject to any disclaimer, the term of this patent is extended or adjusted under 35 U.S.C. 154(b) by 0 days.

(21) Appl. No.: 10/242,322

(22) Filed: Sep. 11, 2002

(65) Prior Publication Data
US 2003/0153774 A1 Aug. 14, 2003

Related U.S. Application Data

(60) Provisional application No. 60/324,821, filed on Sep. 24, 2001.

(51) Int. Cl.$^7$ ............................................. C07C 213/00
(52) U.S. Cl. ....................................... 564/320; 549/467
(58) Field of Search ........................... 564/320; 549/467

(56) References Cited

U.S. PATENT DOCUMENTS 4,136,193 A * 1/1979 Bogeso et al. .............. 514/469
4,650,884 A   3/1987 Bogeso

FOREIGN PATENT DOCUMENTS

WO     WO 00/13648    *  6/2000
WO     WO 01/45483 A2 *  6/2001

OTHER PUBLICATIONS

*Drugs of Future.* 25(6):620–625 (2000).

* cited by examiner

*Primary Examiner*—Bernard Dentz
(74) *Attorney, Agent, or Firm*—Townsend and Townsend & Crew LLP

(57) ABSTRACT

The present invention provides, inter alia, a novel process for the preparation of Citalopram, a known antidepressant.

12 Claims, 5 Drawing Sheets

PROCESS FOR THE PREPARATION OF CITALOPRAM INTERMEDIATE

CROSS-REFERENCE TO RELATED APPLICATION

The present application claims priority to U.S. Provisional Patent Application No. 60/324,821, filed Sep. 24, 2001, the teachings of which are incorporated herein by reference for all purposes.

BACKGROUND OF THE INVENTION

Citalopram is an antidepressant drug that is widely used in both the United States and Europe. Its mode of action and activity have been described in various publications. The active ingredient is an HBr or oxalate salt, preferably an HBr salt. Citalopram has the following structure:

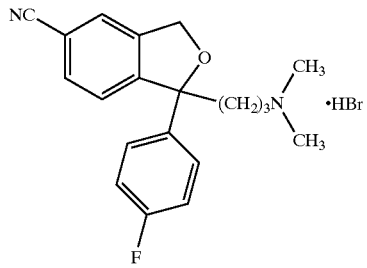

Several processes have been described in the literature for preparing Citalopram (see, *Drugs of Future*, 25(6):620 (2000). Citalopram was first disclosed in German Patent 2,657,271, which is the German equivalent of now expired U.S. Pat. No. 4,136,193. In this patent, 5-bromophthalide (5-BP) was converted via a five-step reaction sequence to Citalopram. This route for preparing Citalopram is depicted in FIG. 1, and constitutes the basis of several patents and patent applications.

Attempts to reproduce the process described in U.S. Pat. No. 4,136,193 for the preparation of Citalopram in the quality specifications required for its use in pharmaceutical applications have been unsuccessful. It is noted that the quality specifications for pharmaceutical quality Citalopram are extremely stringent and require material with purity in excess of 99.7%. Difficulty encountered in manufacturing Citalopram of the required purity by the process described in German Patent No. 2,657,013, U.S. Pat. No. 4,136,193 and PCT International Publication Nos. WO 00/11926 and WO 00/13648 was recently described by Lundbeck in WO 01/45483 A2 (see, page 2, line 26).

Following is the detailed description of the process described in U.S. Pat. No. 4,136,193. It is noted that the experimental process described in U.S. Pat. No. 4,136,193 is for the 4-chlorophenyl analog, but it is noted therein that the process is applicable to the 4-fluorophenyl derivative as well. As illustrated in FIG. 1, the process described in U.S. Pat. No. 4,136,193 involves a 5-step conversion of 5-bromophthalide to Citalopram.

In the first step, a compound of Formula I ("5-BP") is reacted with p-fluorophenyl-magnesium halide; in the second step, the intermediate of a compound of Formula II is isolated and reacted with N,N-dimethylaminopropylmagnesium halide to give the diol of Formula III ("Br-Diol"). The Grignard reaction is conducted in traditional solvents, such as diethyl ether and THF. Unfortunately, the work-up is very complex and involves excessive handling of a flammable liquid, i.e., diethyl ether. The work-up involves the following steps:

The reaction mixture is quenched into ice water;
An aqueous saturated ammonium chloride solution is added;
The mixture is extracted with diethyl ether;
The ether phase is then extracted with 20% aqueous acetic acid;
The acid phase is made alkaline with 10 N aqueous sodium hydroxide;
The aqueous phase is extracted with diethyl ether (2×);
The combined ethereal extracts are dried over anhydrous $K_2CO_3$;
The ether extract is treated with activated carbon; and
The solvent is evaporated in vacuum to give Br-Diol, an oil.

The above work-up process is very laborious and is not suited for large-scale production. Again, it involves the excessive handling of flammable solvents, such as diethyl ether, and it involves numerous unit operations, thereby reducing productivity. Moreover, it is noted that Br-Diol is isolated as the free amine and is an oil. The physical characteristics of Br-Diol are important. Since Br-Diol is an oil, it cannot be isolated as a crystalline solid and, thus, it cannot be purified by techniques such as crystallization/recrystallization. Purification of this oil by crystallization or similar techniques is not described. It is believed that this is one of the major reasons why the process described in U.S. Pat. No. 4,136,193 fails to provide Citalopram in the quality, i.e., purity, required for drug applications. In addition, in order to meet the tight specifications for Citalopram, it is critical that purity is established at this stage.

In step three, Br-Diol is subjected to a ring closure reaction with 60% aqueous phosphoric acid. In a typical reaction, 5-bromophthalide is heated with excess (30 equivalents) 60% aqueous phosphoric acid for 3 h and then neutralized with saturated aqueous ammonia. The resulting mixture is then extracted with diethyl ether, and the ether extract is dried over potassium carbonate. The ether extract is then treated with activated charcoal and stripped of solvent under reduced pressure to give the compound of Formula IV ("5-Br").

As mentioned above, step three employs a large excess of 60% aqueous phosphoric acid. This is troublesome because on reaction completion excess phosphoric acid has to be neutralized with ammonia. Neutralization is an extremely exothermic process and heat management becomes a major issue in the commercial-scale production of this material. In addition, the use of such a large excess of phosphoric acid increases the cost of commercial scale operations due to the use of excess reagents, longer cycle times and reduced loading. Moreover, from a safety point of view, the use of flammable solvents, such as diethyl ether, is discouraged for the commercial-scale production of organic compounds.

In step four, 5-Br is reacted with cuprous cyanide in DMF to give, after the work-up, Citalopram. The reaction conditions and work-up for the process described in U.S. Pat. No. 4,136,193 is as follows:

5-Br is reacted with CuCN in DMF at reflux for 4 h;
The reaction mixture is cooled to 55° C. and quenched into an aqueous solution of ethylene diamine;
The oily layer is separated and the aqueous layer is extracted with benzene;
The combined organic phases are washed with 10% aqueous sodium cyanide;

The organic layer is dried, treated with activated carbon, and concentrated under vacuum to give an oil;

The oil is dissolved in ether and extracted with aqueous acetic acid;

The acetic acid layer is made alkaline with 10 N aqueous sodium hydroxide and extracted with ether; and The ethereal extract is dried over $K_2CO_3$, treated with activated charcoal, and stripped of solvent to give Citalopram.

Unfortunately, there are numerous problems with step four. First, the reaction does not go to completion in 4 h; in reality, conversion after 4 h is <10%. Removal of unreacted 5-Br is difficult and normal purification techniques, such as extraction, crystallization, etc., are not effective. When the reaction is pushed to achieve higher conversion, formation of numerous unidentified side-products is observed. In short, the process described in U.S. Pat. No. 4,136,193 does not work to provide acceptable quality Citalopram. Moreover, the work-up is laborious and involves the use of undesirable solvents such as benzene and diethyl ether.

In the fifth and final step of the process described in U.S. Pat. No. 4,136,193, Citalopram is converted to Citalopram-.HBr or the oxalate salt in the conventional manner—a process is not described for this conversion.

Another route for the preparation of Citalopram has been described in U.S. Pat. No. 4,650,884. This process is based on 5-cyanophthalide ("5-CN"). In this process, 5-CN is reacted with 4-fluorophenylmagnesium halide and N,N-dimethylaminopropylmagnesium halide to give the corresponding hydroxy intermediate that is then dehydrated with sulfuric acid to give Citalopram.

Although a number of processes have been described for the preparation of Citalopram, there remains a need in the art for additional processes that can be prepared in high yield, at the quality specifications required for use in pharmaceutical applications and without the limitations of the prior art method disclosed in now expired U.S. Pat. No. 4,136,193. Quite surprisingly, the present invention fulfills these and other needs.

SUMMARY OF THE INVENTION

The present invention provides a novel process for the preparation of Citaopram and, in particular, Citalopram.HBr. Using the process of the present invention, Citalopram.HBr can be readily prepared in high yields, at the quality specifications required for use in pharmaceutical applications (i.e., greater than 99.7% pure) and without the limitations of the prior art methods.

Other features, objects and advantages of the invention and its preferred embodiments will become apparent from the detailed description which follows.

DETAILED DESCRIPTION OF THE INVENTION AND PREFERRED EMBODIMENTS

Figure 2:
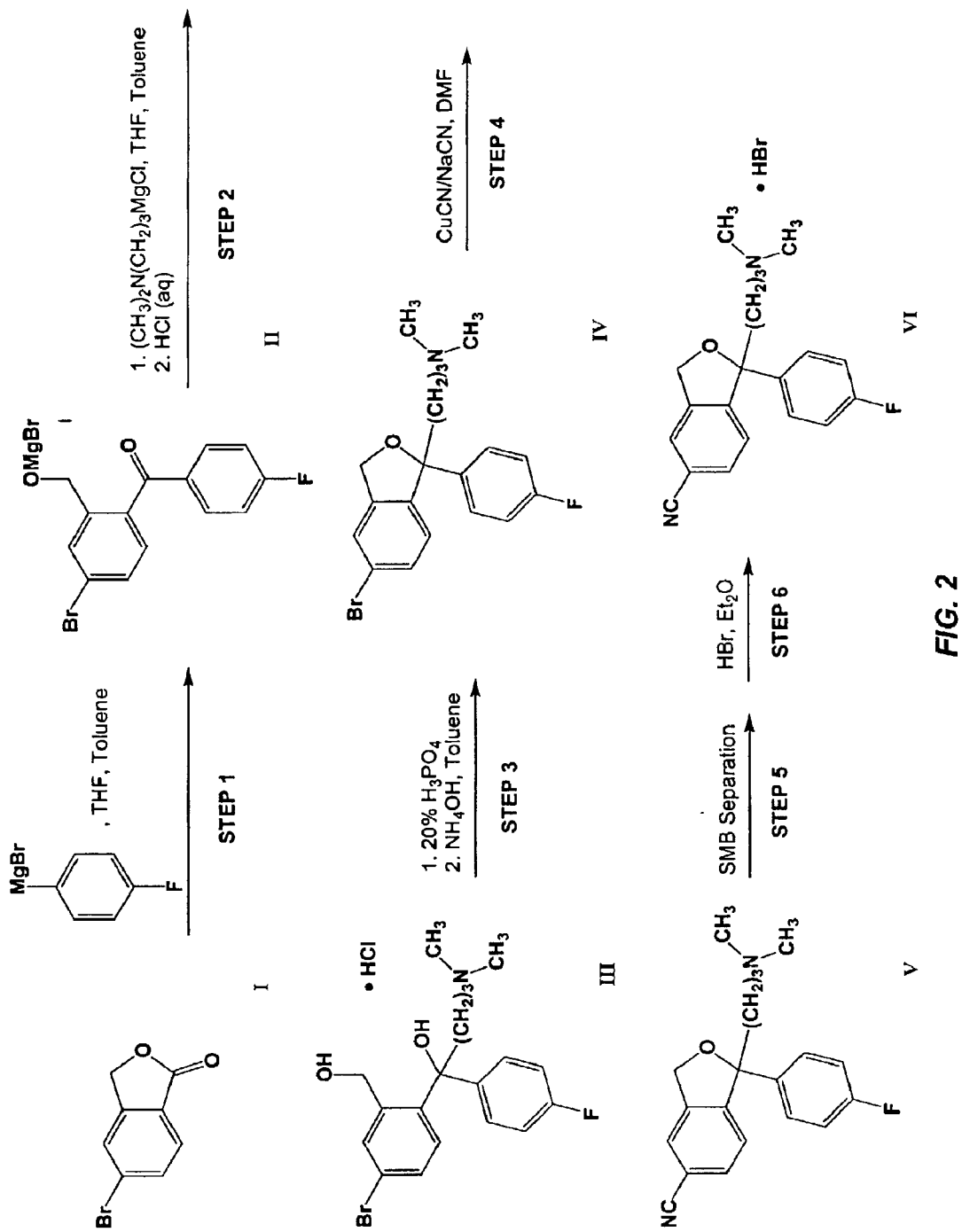
FIG. 2 illustrates a process in accordance with one aspect of the present invention that can be used to prepare Citalopram in high yield and at the quality specifications required for use in pharmaceutical applications.

The present invention provides a process for the preparation of Citalopram and, in particular, Citalopram.HBr. FIG. 2 illustrates an exemplary process for the preparation of Citalopram.HBr in accordance with the present invention.

Figure 1:
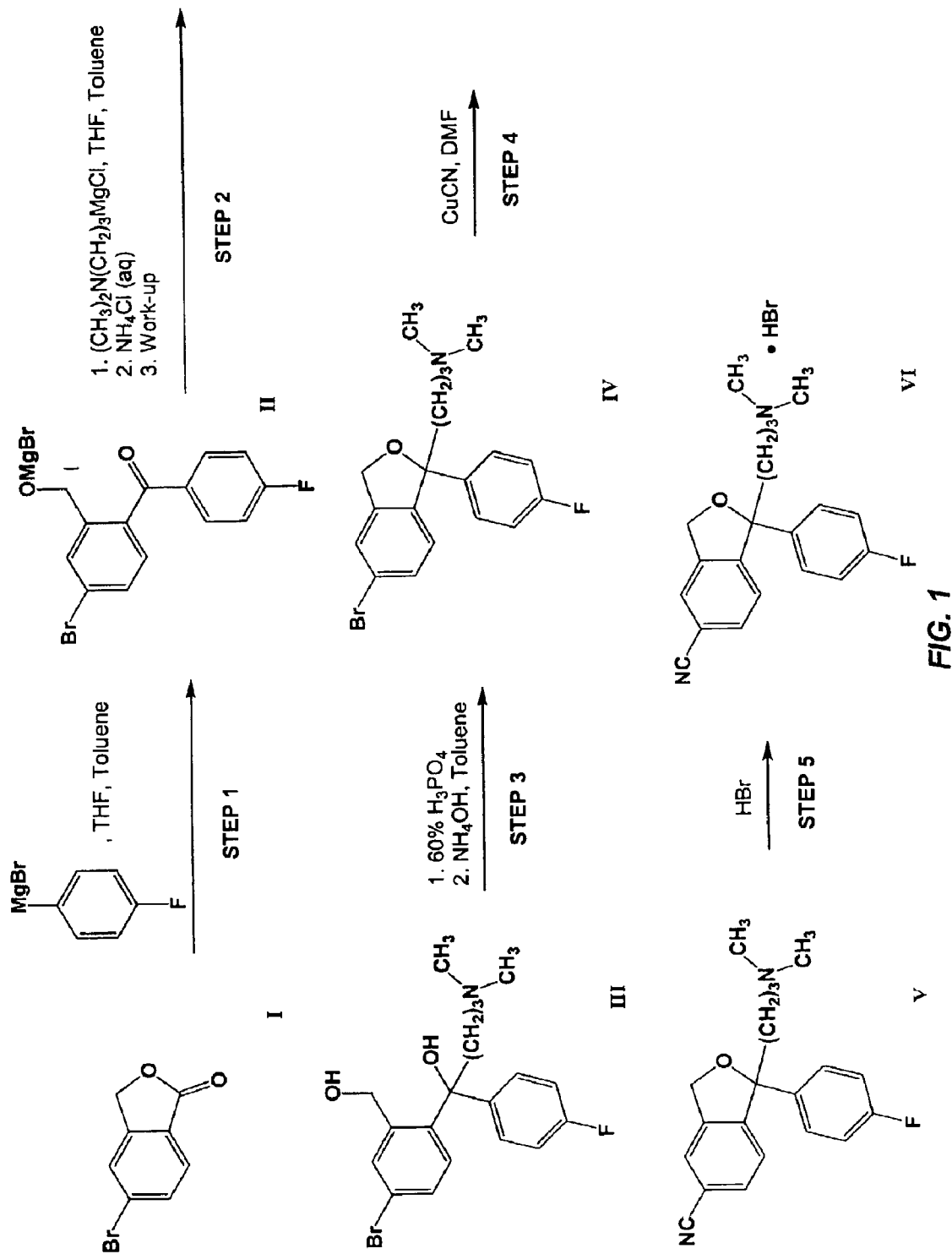
FIG. 1 illustrates a prior art process used to prepare Citalopram. This process was originally disclosed in now expired U.S. Pat. No. 4,136,193.

As illustrated in FIG. 1, the present invention provides a salt of the compound of Formula III, which can be isolated as a crystalline material, and a novel, simplified process for preparing such salt. The ability to isolate a salt of the compound of Formula III allows one to set the purity at this step by allowing one to get rid of impurities that would otherwise be carried through the process, making it impossible to prepare high quality Citalopram.

As such, in one embodiment, the present invention provides a crystalline salt of the compound of Formula III having the following structure:

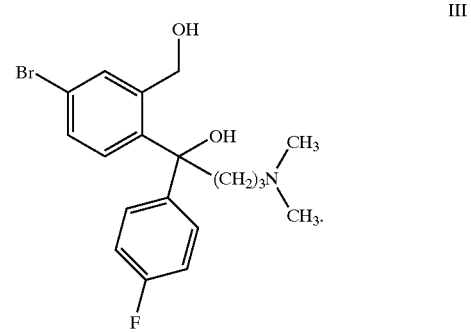

In a presently preferred embodiment, the crystalline salt is an acid salt. Suitable acid salts include, but are not limited to, a HCl salt, a HBr salt, a $H_2SO_4$ salt, a $H_3PO_4$ salt, a methanesulfonic acid salt, a trifluoroacetic acid salt, an acetic acid salt, a fumaric acid salt and a citric acid salt. In a presently preferred embodiment, the crystalline salt is an HCl salt having the following structure:

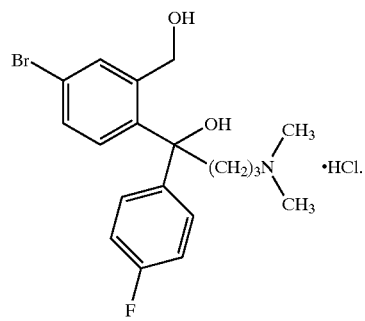

In another aspect, the present invention provides a method for preparing the salt of the compound of Formula III, the process comprising: (a) contacting a compound of Formula I having the following structure:

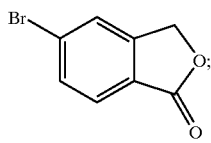

with 4-fluorophenyl magnesium bromide to form an intermediate of Formula II having the following structure:

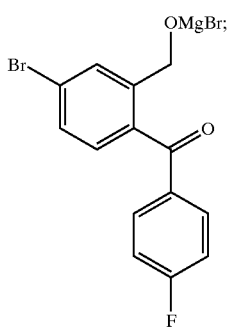

(b) contacting the intermediate of Formula II with dimethylaminopropyl magnesium chloride in an organic solvent to form a reaction mixture; and (c) quenching the reaction mixture with an acid to form a product mixture comprising the salt of the compound of Formula III. In one embodiment of the above process, the crystalline salt is an acid salt. Suitable acid salts include, but are not limited to, a HCl salt, a HBr salt, a $H_2SO_4$ salt, a $H_3PO_4$ salt, a methanesulfonic acid salt, a trifluoroacetic acid salt, an acetic acid salt, a fumaric acid salt and a citric acid salt. In a presently preferred embodiment, the crystalline salt is an HCl salt having the following structure:

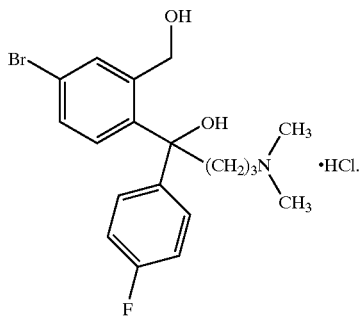

In connection with this particular embodiment, it has been surprisingly found that depending on the isolation and recrystallization procedures used to isolate the HCl salt of the compound of Formula III, different polymorphs are obtained. For instance, the crude HCl salt of the compound of Formula III, isolated from a mixture of THF/toluene/aqueous HCl has one melting point, whereas the crude HCl salt of the compound of Formula III recrystallized from butanol has a second melting point.

As such, in one embodiment, the acid used in step (c) is a member selected from the group consisting of HCl, HBr, $H_2SO_4$, $H_3PO_4$, methanesulfonic acid, trifluoroacetic acid, acetic acid, fumaric acid and citric acid. Again, in a preferred embodiment, the acid is aqueous HCl.

In one embodiment, the solvent used in step (b) is an organic solvent. Suitable organic solvents include, but are not limited to, diethylether, t-butylmethylether, THF, dioxane, toluene, xylene and mixtures thereof. In a preferred embodiment, the organic solvent used in step (b) is a mixture of THF and toluene.

In a preferred embodiment, the above method further comprises: (d) isolating the salt of the compound of Formula III from the product mixture. In one embodiment, step (d) comprises: (i) filtering the product mixture to obtain the salt of the compound of Formula III. In another embodiment, step (d) further comprises: (ii) washing the salt of the compound of Formula III with water and toluene. In yet another embodiment, step (d) further comprises: (iii) recrystallizing the salt of the compound of Formula III from a member selected from the group consisting of 1-butanol, 2-butanol and water. In a preferred embodiment, the salt of the compound of Formula III is recrystallized from 2-butanol.

In another aspect, the present invention provides a method for preparing a compound of Formula IV having the following structure:

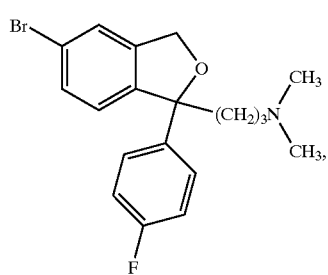

the method comprising: (a) contacting a salt of the compound of Formula III having the following structure:

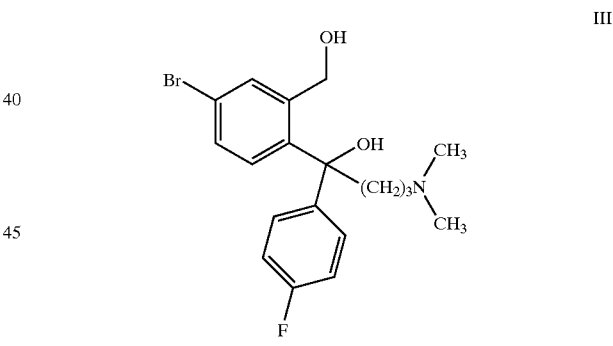

with about 2 to about 10 equivalents of phosphoric acid to form a reaction mixture; (b) adding an organic solvent to said reaction mixture; and (c) quenching said reaction mixture with base to form a product mixture comprising said compound of Formula IV.

With respect to this method, the patent literature (e.g., U.S. Pat. No. 4,136,193) teaches that an excess of 60% phosphoric acid (~30 equivalents) is required in order to achieve ring closure. However, it has now been surprisingly found that ring closure can be achieved with significantly fewer equivalents of phosphoric acid (e.g., about 2 to about 10 equivalents). This finding gives rise to a purer product and numerous other advantages. For instance, one of the problems associated with the process disclosed in U.S. Pat. No. 4,136,193 for making Citalopram is neutralization of excess phosphoric acid with ammonia. As expected, this reaction is very exothermic and takes a long time to neutralize the reaction mixture. Long neutralization time equates to longer cycle time, which in turn means lower productivity. Since fewer equivalents of phosphoric acid are used and the amount of ammonia needed to quench the excess phosphoric acid is reduced, the overall batch size is higher than the normal batch size by nearly 20%. As such, the method of the present invention provides purer product, is more suited for commercial scale production, and has much higher productivity.

In one embodiment, the salt of the compound of Formula III is a HCl salt. In another embodiment, the phosphoric acid is about 20% to about 60% phosphoric acid. In a preferred embodiment, the compound of Formula III is contacted with about 6 to about 9 equivalents of 20% phosphoric acid. In another preferred embodiment, the compound of Formula III is contacted with about 9 equivalents of 20% phosphoric acid. It will be readily apparent to those of skill in the art that other acids can be used in place of phosphoric acid. Suitable acids include, but are not limited to, HCl, HBr, sulfuric acid, trifluoroacetic acid, and methane sulfonic acid, etc.

In another embodiment, the organic solvent in step (b) is a member selected from the group consisting of toluene, benzene, xylene, diethylether, t-butylmethylether, dioxane, and mixtures thereof. In a preferred embodiment, the organic solvent in step (b) is toluene.

In another embodiment, the base is a member selected from the group consisting of ammonium hydroxide, sodium hydroxide and potassium hydroxide. In a presently preferred embodiment, the base is aqueous ammonium hydroxide.

In a preferred embodiment, the above method further comprises: (c) isolating the compound of Formula IV from the product mixture. In one embodiment, step (c) comprises: (i) separating the organic phase and the aqueous phase; (ii) re-extracting the aqueous phase with toluene; (iii) combining the organic phases to form a combined organic phase and washing the combined organic phase with water; and (iv) distilling the washed organic phase to obtain the compound of Formula IV.

In a preferred embodiment, the above method is carried out at a temperature of about 80° C.±10° C.

In another aspect, the present invention provides a method for preparing a compound of Formula V having the following structure:

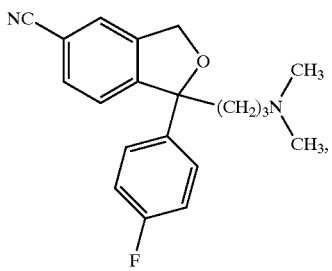

V the method comprising: (a) contacting a compound of Formula IV having the following structure:

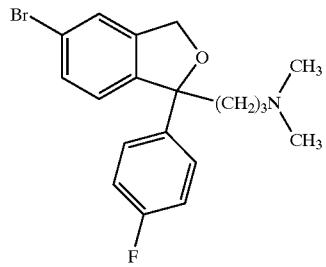

IV with a mixture of cuprous cyanide and sodium cyanide to form a reaction mixture; (b) heating the reaction mixture until the reaction is complete; and (c) quenching the reaction mixture to form a product mixture comprising the compound of Formula V. It has been found that a mixture of cyanating agents works surprisingly well for carrying out this method.

In one embodiment, the compound of Formula IV is in a first organic solvent. Suitable first organic solvents include, but are not limited to, toluene, benzene, xylene, diethylether, t-butylmethylether, dioxane, and mixtures thereof. In a preferred embodiment, the first organic solvent is toluene. In another embodiment, the mixture of cuprous cyanide and sodium cyanide is in a second organic solvent. Suitable second organic solvents include, but are not limited to, N,N-dimethylformamide, N,N-dimethylacetamide, N-methylpyrrolidione, quinoline, collidine, xylene, dimethylsulfone, hexamethylphosphoramide and trifluoromethylchlorobenzene. In a preferred embodiment, the second organic solvent is N,N-dimethylformamide.

It will be readily apparent to those of skill in the art that the ratio of cuprous cyanide:sodium cyanide in the mixture of cuprous cyanide and sodium cyanide can be varied. In a presently preferred embodiment, the ratio of cuprous cyanide:sodium cyanide in the mixture of cuprous cyanide and sodium cyanide is about 2.5:1.0 to about 1:2.5. In a presently preferred embodiment, the ratio of cuprous cyanide:sodium cyanide in the mixture of cuprous cyanide and sodium cyanide is about 0.50:1.0 to about 2.5:1. In another preferred embodiment, the ratio of cuprous cyanide:sodium cyanide in the mixture of cuprous cyanide and sodium cyanide is about 0.75:1.0 to about 1.0:1.0. It will be readily apparent to those of skill in the art that other mixtures of cyanating agents (e.g., KCN:CuCN or Metal-CN:CuCN complexes) can be used in the above method of the present invention.

In one embodiment, the first organic solvent is removed from the reaction mixture prior to step (b). In another embodiment, the reaction mixture is quenched with a member selected from the group consisting of aqueous sodium cyanide and aqueous potassium cyanide. In a preferred embodiment, the reaction mixture is quenched with 10% aqueous sodium cyanide.

In a preferred embodiment, the above method further comprises: (d) isolating the compound of Formula V from the product mixture. In one embodiment, step (d) comprises: (i) adding ethylenediamine and a first organic solvent to the reaction mixture and separating the organic phase and the aqueous phase; (ii) re-extracting the aqueous phase with the first organic solvent; (iii) combining the organic phases to form a combined organic phase and back-extracting the combined organic phase with an acid to form an acid extract; (iv) neutralizing the acid extract with a base to a pH of about 8.5 to about 11 to form a neutralized extract; (v) extracting the neutralized extract with a second organic solvent to form a second organic solvent extract; (vi) treating the second organic solvent extract with charcoal and removing the second organic solvent to generate the compound of Formula V.

In a preferred embodiment of step (d), the first and second organic solvents are independently selected from the group consisting of toluene, benzene, xylene, diethylether, t-butylmethylether, dioxane, and mixtures thereof. In another preferred embodiment, the first and second organic solvents are both toluene.

In one embodiment, the acid in step (iii) is a member selected from the group consisting of HCl, HBr, $H_2SO_4$, $H_3PO_4$, trifluoroacetic acid and acetic acid. In a preferred embodiment, the acid in step (iii) is 20% aqueous acetic acid. In one embodiment, the base in step (iv) is a member selected from the group consisting of sodium hydroxide, potassium hydroxide and sodium carbonate. In a preferred embodiment, the base in step (iv) is sodium hydroxide. In one embodiment, the acid extract in step (iv) is neutralized with the base to a pH of about 9 to about 10.

In another aspect, the above method further comprises purifying the compound of Formula V using simulated moving bed (SMB) chromatography having a stationary phase and a mobile phase. It has been found that SMB chromatography works surprisingly well for removing non-polar impurities found in the reaction mixture. In one embodiment, the stationary phase is a reverse phase silica gel and the mobile phase is an organic solvent/water mixture. A C18-derivatized silica gel is an example of a suitable reverse phase silica gel. Typically, the pH of the mobile phase is about 1.5 to about 4.0, more preferably about 2.5. The pH of the mobile phase can be maintained by, for example, the addition of 0.1 to 2% trifluoroacetic acid. In a preferred embodiment, the organic solvent in the mobile phase is methanol. In another preferred embodiment, the organic solvent in the mobile phase is ethanol. In another preferred embodiment, the organic solvent in the mobile phase is acetonitrile.

In another embodiment, the stationary phase is a normal phase silica gel and the mobile phase is an organic solvent mixture. In one embodiment, the organic solvent mixture is a mixture of an alcohol, a hydrocarbon and an organic base. Suitable alcohols include, but are not limited to, methanol, ethanol, n-propanol and isopropanol. Suitable hydrocarbons include, but are not limited to, heptane, n-heptane, hexane, isohexane, toluene, cyclohexane, benzene and combinations thereof. Suitable organic bases include, but are not limited to, triethylamine, diethylamine, trimetylamine, dimethylamine, tripropylamine, tributylamine, diisopropylethylamine, dicyclohexylamine and diethylisopropylamine. In a preferred embodiment, the organic base is present in the organic solvent mixture at about 0.05 to about 5%, more preferably at about 0.1 to about 0.5% and, even more preferably, at about 0.2 to about 0.4%. In a preferred embodiment, the organic solvent mixture is a mixture of ethanol, heptane and triethylamine.

In another embodiment, the stationary phase is a chiral phase silica gel and the mobile phase is an organic solvent mixture. Suitable chiral phase silica gel stationary phases include, but are not limited to, CHIRALPAK® AD™; CHIRALPAK® AS™; CHIRALCEL® OD™; and CHIRALCEL® OJ™, all of which are commercially available from Daicel, through its subsidiary, Chiral Technologies Inc. In one embodiment, the organic solvent mixture is a mixture of an alcohol (which may or may not be denatured with, for example, a hydrocarbon such as n-heptane), a hydrocarbon and an organic base. Suitable alcohols include, but are not limited to, methanol, ethanol, n-propanol and isopropanol. Suitable hydrocarbons include, but are not limited to, heptane, n-heptane, hexane, isohexane, toluene, cyclohexane, benzene and combinations thereof. Suitable organic bases include, but are not limited to, triethylamine, diethylamine, trimetylamine, dimethylamine, tripropylamine, tributylamine, diisopropylethylamine, dicyclohexylamine and diethylisopropylamine. In a preferred embodiment, the organic base is present in the organic solvent mixture at about 0.05 to about 5%, more preferably at about 0.1 to about 0.5% and, even more preferably, at about 0.2 to about 0.4%. In a preferred embodiment, the organic solvent mixture is a mixture of ethanol, heptane and triethylamine.

In another embodiment, the compound of Formula V is further purified using single column chromatography having a stationary phase and a mobile phase. It has been found that single column chromatography works surprisingly well for removing any non-polar impurities found in the reaction mixture. Suitable stationary and mobile phases are similar to those described above in connection with the SMB chromatography.

In another aspect, the present invention provides a method for preparing a compound of Formula VI having the following structure:

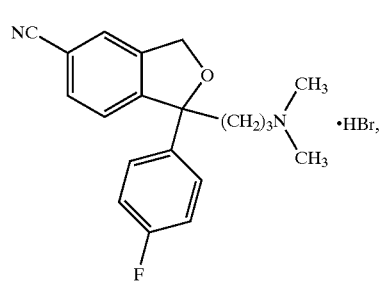

VI the method comprising: (a) dissolving a compound of Formula V having the following structure:

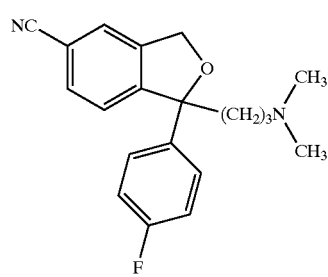

V in an organic solvent to form a reaction mixture; and (b) contacting the reaction mixture with HBr to form a product mixture comprising the compound of Formula VI.

In one embodiment, the organic solvent in step (a) is a member selected from the group consisting of acetone, methylethylketone, ethylacetate, toluene, benzene, xylene, diethylether, t-butylmethylether, dioxane, and mixtures thereof. In a preferred embodiment, the organic solvent in step (a) is diethylether. In another preferred embodiment, the organic solvent in step (a) is acetone.

In one embodiment, the HBr is gaseous HBr. In an example of this embodiment, the method comprises bubbling gaseous HBr into the reaction mixture to form a product mixture comprising the compound of Formula VI. In another embodiment, the HBr is aqueous HBr and the reaction mixture is contacted with aqueous HBr to form a product mixture comprising the compound of Formula VI.

In a preferred embodiment, the above method further comprises: (c) isolating the compound of Formula VI from the product mixture. In one embodiment, step (c) comprises: (i) cooling the product mixture and filtering the product mixture to obtain the compound of Formula VI as a precipitated solid; (ii) washing the precipitated solid with an organic solvent; and (iii) drying the precipitated solid to obtain the compound of Formula VI. In one embodiment, step (c) further comprises: (iv) recrystallizing the compound of Formula VI. In one embodiment, the compound of Formula VI is recrystallized from a solvent mixture of toluene and methanol. In another embodiment, the compound of Formula VI is recrystallized from a solvent mixture of methanol and isopropylalcohol (IPA).

In another embodiment, step (iv) comprises: (i') combining the precipitated solid with toluene and methanol to form a mixture and heating the mixture; (ii') filtering the mixture through Celite and slowly cooling the mixture; and (iii') filtering the mixture to obtain the crystallized solid, washing the crystallized solid with toluene, and drying the crystallized solid to obtain the compound of Formula VI. In one embodiment, in step (ii'), the mixture is cooled to about ambient temperature. In another embodiment, in step (ii'), the mixture is cooled to about 0° C. to about 5° C.

In yet another embodiment, step (iv) comprises: (i') combining the precipitated solid with methanol and isopropylalcohol (IPA) to form a mixture and heating the mixture; (ii') filtering the mixture through Celite and slowly cooling the mixture; and (iii') filtering the mixture to obtain the crystallized solid, washing the crystallized solid with isopropylalcohol, and drying the crystallized solid to obtain the compound of Formula VI. In one embodiment, in step (ii'), the mixture is cooled to about ambient temperature. In another embodiment, in step (ii'), the mixture is cooled to about 0° C. to about 5° C.

In another embodiment, the present invention provides a process for the removal of demethyl-(A) and didemethyl-(B) impurities from crude Citalopram mixtures, wherein the demethyl- and didemethyl-impurities have the following structures:

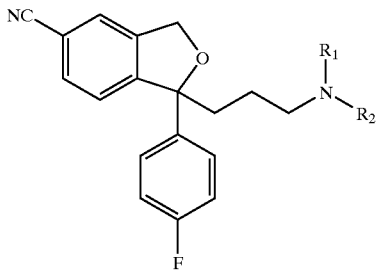

A: $R_1=R_2=H$

B: $R_1=H, R_2=CH_3$

Demethyl-(A) and didemethyl-(B) impurities are common impurities formed at various stages during the preparation of Citalopram. Unfortunately, these troublesome impurities present a challenge in removal due to their structural proximity to Citalopram.

As such, the present invention provides a method for removing demethyl- and didemethyl-impurities from a crude Citalopram mixture containing demethyl- and didemethyl-impurities in a solvent, the method comprising: (a) contacting the mixture of Citalopram with a scavenger resin having a functional group that is reactive with a primary or secondary amine to form resin-bound demethyl- and/or didemethyl-impurities, wherein the scavenger resin is insoluble in the solvent; and (b) filtering the resin-bound demethyl- and/or didemethyl-impurities, thereby removing the demethyl and/or didemethyl-impurities from the mixture of Citalopram.

In one embodiment of the above method, the functional group on the scavenger resin includes, but is not limited to, isocyanates, isothiocyanates, acid chlorides, esters and anhydrides. In some embodiment, the scavenger resin can have more than one functional group and, in this case, the functional groups can be the same or different. It has been found that such functional groups react with the primary and/or secondary amine functionalities present in impurities A and B, virtually in an irreversible fashion, thereby attaching impurities A and B to the scavenger resin. The attachment of impurities A and B to the scavenger resin renders such impurities insoluble as well.

The scavenger resin can be any resin that (1) is insoluble in the solvent in which the product is dissolved; (2) is non-reactive with the solvent in which the product is dissolved; and (3) contains a functional group that is reactive with a primary and/or a secondary amine. In one embodiment, the scavenger resin is a polystyrene-based resin. In another embodiment, the scavenger resin is a silica gel-based resin. In a preferred embodiment, the scavenger resin is a polystyrene-based resin having the following structure:

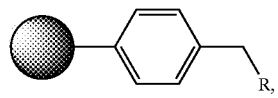

wherein: R is a functional group that is reactive with a primary and/or secondary amine such as those described above.

The above method is typically carried out by stirring a crude Citalopram mixture containing A and/or B in an appropriate solvent with a scavenger resin having a functional group that is reactive with the primary and/or secondary amine functionalities present in A and B, respectively. Suitable solvents include, but are not limited to, toluene, benzene, xylene, diethylether, t-butylmethylether, dioxane, and mixtures thereof. The resulting mixture is a heterogeneous mixture as the scavenger resin is also insoluble in the solvent. It is thought that impurities A and B, but not Citalopram, attach to the resin by making a covalent bond between a primary or secondary amine functionality and the functional group on the scavenger resin, thereby rendering them insoluble. A simple filtration of the resin-bound, i.e., insoluble, impurities A and B affords a purified Citalopram solution virtually free of impurities A and B.

The above method has a number of significant advantages including, but not limited to, the following: (1) it selectively renders otherwise soluble impurities A and B insoluble by binding them to the insoluble resin through the reaction of the reactive end groups of the scavenger resin and the primary and secondary amine functionalities present in impurities A and B; (2) the scavenger resin will bind any other impurity containing a primary or secondary amine functionalities and render them insoluble as well; (3) the scavenger resin cannot react with the desired Citalopram, which has a tertiary amine functionality; (4) once the resin binds to the impurities A, B (or any other impurity containing a primary or secondary amine functionality) rendering them insoluble, only a simple filtration is required to remove these impurities, thereby minimizing any loss (i.e., any loss due to the acid/base wash and/or crystallization and recrystallization utilized in the method disclosed in PCT Patent Publication No. WO 01/45483 A2); and (5) once the filtration is performed, a purified Citalopram solution is obtained and the purified Citalopram can be recovered by a simple evaporation of the solvent.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

EXAMPLES

A. Preparation of Dimetlylaminopropyl Magnesium Chloride

A 30% aqueous sodium hydroxide (1.04 kg, 7.80 mol, 1.10 eq.) solution was added to a mixture of 65% aqueous dimethylaminopropyl chloride hydrochloride (1.71 kg, 7.04 mol, 1.00 eq.) and toluene (0.167 kg) at <20° C.

The phases were separated.

The organic phase was combined with THF (0.600 kg) and dried over molecular sieves (Siliporite NK10, 0.227 kg).

Approximately 5% of the dried dimethylaminopropyl chloride solution was added to a mixture of magnesium (0.170 kg, 7.00 mol, 1.00 eq.), ethyl bromide (0.0038 kg, 0.035 mol, 0.0050 eq.), and THF (1.60 kg).

The resulting mixture was heated to reflux (>68° C.) and the remaining dimethylaminopropyl chloride solution was added over 1.5 h.

Reflux (>68° C.) was maintained throughout the addition period by adjusting the addition rate and heating and/or cooling as necessary.

The mixture was refluxed (>70° C.) for 1 h, then cooled to ambient temperature and stored under a dry nitrogen atmosphere.

B. Preparation of (4-Bromo-2-hydroxymethyl) phenyl-(4-fluorophenyl)-(3-dimethylaminopropyl) Methanol Hydrochloride A solution of 1.1 M 4-fluorophenyl magnesium bromide in THF (5.57 kg, 6.01 mol, 1.28 eq.) was added to a mixture of 5-bromophthalide (1.00 kg, 4.69 mol, 1.00 eq), and toluene (6.25 kg) at <20° C. over 1 h.

The mixture was stirred at <20° C. for 0.5 h.

A solution of 1.8 M dimethylaminopropyl magnesium chloride (3.90 kg, 7.02 mol, 1.50 eq.) was added to the mixture over 2 h, maintaining <30° C. with cooling.

The resulting mixture was stirred ambient temperature for 16 h.

The mixture was quenched into 6.23% aqueous hydrochloric acid (9.9 kg, 19.3 mol, 4.1 eq.).

The slurry was stirred at ambient temperature for 1 h and filtered.

The product was then washed with water (2.00 kg) and toluene (4.00 kg).

The off-white solids were dried at 35–40° C. under vacuum to yield 1.63 kg (80.4% yield) of crude bromodiol*HCl.

C. Purification of Bromodiol HCl

A mixture of crude bromodiol*HCl (1.60 kg) and 2-butanol (8.00 kg) was heated to 70° C. to form a hazy solution and filtered through a bed of celite.

The resulting solution was cooled slowly to 5° C. to precipitate the product.

The resulting slurry was filtered and washed with 2-butanol (1.60 kg).

The off-white solids were dried at 35–40° C. under vacuum to yield 1.18 kg (73.8% recovery from crude) of bromodiol*HCl.

The properties of the Bromodiol*HCl are as follows:
HPLC area % purity: 99.9%.
mp (DSC): 183° C.
$^1$H NMR (d-DMSO): δ10.19 (s, 1H), δ7.0–7.8 (m, 7H), δ5.90 (s, 1H), δ5.17 (s, 1H), δ4.49 (d, 1H), δ3.97 (d, 1H), δ3.02 (m, 2H), δ2.65 (s, 6H), δ2.21 (m, 2H), δ1.65 (m, 1H), δ1.36 (m, 1H).

D. Preparation of 5-Bromo-1-(4-fluorophenyl)-1-(3-dimethylaminopropyl)-phthalan ("5-Br")

A mixture of bromodiol*HCl (1.12 kg, 2.59 mol, 1.00 eq.) and 60% phosphoric acid (12.7 kg, 77.8 mol, 30.0 eq.) was heated to 90° C. for 1 h.

The mixture was cooled to <10° C.

Toluene (6.72 kg) and water (8.96 kg) were added to the solution and the mixture was quenched with 28% aqueous ammonium hydroxide (9.37 kg, 74.9 mol, 28.9 eq.), maintaining <25° C.

The phases were separated and the aqueous layer was re-extracted with toluene (4.48 kg).

The organic phases were combined and washed with water (4.0 kg).

The solvent was distilled from the washed organic extracts to yield 977 g (99.2% yield, 95.2% yield corrected for residual solvents) of 5-Br as an orange oil.

The properties of 5-Br are as follows:
HPLC area % purity: 99.0%.
$^1$H NMR (d-DMSO): δ7.1–7.6 (m, 7H), δ5.10 (m, 2H), δ2.51 (m, 2H), δ2.11 (m, 2H), δ2.01 (s, 6H), δ1.23 (m, 2H).

E. Modified Process for the Preparation of 5-Br

A mixture of bromodiol*HCl (0.200 kg, 0.462 mol, 1.00 eq.) and 20% phosphoric acid (2.04 kg, 4.16 mol, 9.00 eq.) was heated to 90° C. for 2.5 h.

The mixture was cooled to <10° C.

Toluene (1.20 kg) was added to the solution and the mixture was quenched with 28% aqueous ammonium hydroxide (0.574 kg, 4.59 mol, 9.93 eq.), maintaining <25° C.

The phases were separated and the aqueous layer was re-extracted with toluene (0.800 kg).

The organic phases were combined and washed with water (0.800 kg).

The solvent was distilled from the washed organic extracts to yield 164 g (93.6% yield) of 5-Br as an orange oil.

The properties of 5-Br are as follows:
HPLC area % purity: 99.2%.
$^1$H NMR (d-DMSO): δ7.1–7.6 (m, 7H), δ5.10 (m, 2H), δ2.51 (m, 2H), δ2.11 (m, 2H), δ2.01 (s, 6H), δ1.23 (m, 2H).

F. Process for the Preparation of 5-Cyano-1-(3-dimethylaminopropyl)-1-(p-fluorophenyl)phthalane ("Citalopram" or "5-CN")

A solution of 5-bromo-1-(3-dimethylaminopropyl)1-(p-fluorophenyl)phthalane (100.5 g, 0.266 mol) in toluene was added to a mixture of cuprous cyanide (50.0 g, 0.558 mol) and sodium cyanide (9.8 g, 0.200 mol) in of N,N-dimethylformamide (450 mL)

Toluene was removed by distillation and the resulting mixture was heated to 154–159° C. under nitrogen until the desired conversion was achieved.

The reaction mixture was then chilled to 60–70° C. and quenched with a 10% aqueous NaCN solution (350 g).

Aqueous ethylenediamine (41% solution, 140 g) and toluene (500 mL) were added and the mixture was filtered.

The organic layer was separated and the aqueous layer was extracted with toluene (2×100 mL).

The combined organic extracts were washed with water (2×100 mL).

The organic extract was then extracted with 20% acetic acid solution (2×250 mL).

The combined acetic acid extracts were neutralized with 16.6% aqueous NaOH to a pH of about 9 to about 10 and extracted with toluene (3×300 mL).

The combined toluene extracts were treated with activated charcoal (16.1 g) and stripped of solvent under reduced pressure to give crude Citalopram (72.3 g, 84%) as a light brown oil.

The properties of 5-CN are as follows:
HPLC purity: 95% with 5% unreacted 5-Br.
$^1$H NMR (DMSO-$d_6$): δ7.6 (s, 1H, 4-H aromatic proton), 6.98 to 7.52 (m, 6H, aromatic protons), 5.25 (d, 1H, 3-H$_a$), 5.15 (d, 1H, 3-H$_b$), 3.08 (t, 2H, 3'-CH$_2$), 2.71 (s, 6H, —N(CH$_3$)$_2$), 2.49 to 2.27 (m, 2H, 1'-CH$_2$), 1.82 to 1.71 (m, 2H, 2'-CH$_2$);
LC/MS: m/z, 325 (M+1).

G. Process for the Purification of Crude 5-CN

The crude 5-CN product is dissolved in a mixture of heptane/ethanol/TEA (90%:10%:0.1%), and separated using Multi-Column Chromatography (MCC) equipment (SMB) to provide 5-CN with <0.1% 5-Br. The mobile phase is heptane/ethanol/TFA. The stationary phase is CHIRALCEL OD™. MCC separation has been demonstrated on 400 g scale and the product isolated from the separation was >99.9% pure. The product was so pure that when it was converted to the HBr salt, it maintained its purity and did not require additional purification—a 20% savings in the yield.

H. Process for the Preparation of 5-Cyano-1-(3-dimethlylaminopropyl)-1-(p-fluorophenyl)phthalane HBr (Citalopram-HBr)

HBr gas (18.0 g, 0.223 mol) was bubbled into a stirred solution of pure 5-CN (72.3 g, 0.223 mol) in 723 mL acetone at 20–25° C.

The resulting slurry was cooled to 0–5° C. and filtered.

The product was washed with cold acetone (3×100 mL) and dried in vacuo (60–80° C. at 5–10 mmHg) to give Citalopram-HBr (69.8 g, 77.3%), a white solid.

I. Purification of Citalopram-HBr

A mixture of the crude product (69.8 g), toluene (1117 g), and methanol (138 g) was heated to 60–70° C.

The resulting solution was filtered through celite and slowly cooled to ambient temperature.

The crystallized solid was filtered, washed with 100 mL toluene, and dried in vacuo (60–80° C. at 10 mmHg) to give pure Citalopram-HBr (53.2 g, 76.2%), a white solid.

The properties of Citalopram-HBr are as follows:
mp (DSC): 186° C.
HPLC Purity: 99.8%.
IR (KBr): 2931, 2655, 2229, 1507, 1217, 1028, 1013, 835 cm$^{-1}$;
$^1$H NMR (DMSO-$d_6$): δ9.15 (s, 1H, —NH(CH$_3$)$_2$), 7.71 to 7.91 (m, 3H, aromatic protons), 7.52 to 7.64 (m, 2H, aromatic protons), 7.06 to 7.27 (m, 2H, aromatic protons), 5.08 to 5.28 (q, 2H, 3-H), 3.3 (t, 2H, 3'-CH$_2$), 2.65 (s, 6H, —NH(CH$_3$)$_2$), 2.2 (t, 2H, 1'-CH$_2$), 1.29 to 1.60 (m, 2H, 2'-CH$_2$).

J. Process for the Preparation of 5-Cyano-1-(3-dimethylaminopropyl)-1-(p-fluorophenyl)phthalane HBr (Citalopram-HBr)

In addition to the foregoing method, Citalopram.HBr can be prepared using aqueous HBr. It has been found that the resulting product prepared using aqueous HBr is equivalent to that prepared using gaseous HBr in both yield and purity.

C.HBr Salt Formation

48% HBr (aq) (54.1 g, 0.321 mol) is added to a stirred solution of 5-CN (104.1 g, 0.31 mol) in Toluene (366 g) at 5–10° C.

The resulting slurry is cooled to 0–5° C. and filtered.

The product is washed with cold Toluene (2×107 mL) and dried in vacuo (60–80° C. at 5–10 mm Hg) to afford C-HBr (97.5 g, 93.6%) as a white solid.

Recrystallization/Purification

A recrystallization is not necessary when using 5-CN purified by SMB chromatography. However, the following can be performed if further purification is required or desired.

A mixture of C-HBr (97.5 g, 0.301 mol), methanol (103.6 g) and isopropanol (207.2 g) is heated to 60–70° C.

The resulting solution was cooled to 0° C. and filtered.

The recrystallized product was washed with cold isopropanol (2×75 mL) and dried in vacuo (60–80° C. at 5–10 mm Hg) to afford C-HBr (88.6 g, 85.1%) as a white solid.

The properties/characterization of pure C-HBr are as follows:

| | |
|---|---|
| mp (DSC): | 187° C. |
| HPLC Purity: | 99.8% |
| 5-Br: | None detected |
| Total Impurities: | ≦0.2% |
| Unknown Inpurities ≦0.1%: | None detected |
| IR (KBr): | 2931, 2655, 2229, 1507, 1217, 1028, 1013, 835 cm$^{-1}$; |
| $^1$H NMR (DMSO-$d_6$): | δ 9.15 (s, 1H, —NH(CH$_3$)$_2$), 7.71 to 7.91 (m, 3H, aromatic protons), 7.52 to 7.64 (m, 2H, aromatic protons), 7.06 to 7.27 (m, 2H, aromatic protons), 5.08 to 5.28 (q, 2H, 3-H), 3.3 (t, 2H, 3'-CH$_2$), 2.65 (s, 6H, —NH(CH$_3$)$_2$), 2.2 (t, 2H, 1'-CH$_2$), 1.29 to 1.60 (m, 2H, 2'-CH$_2$). |

K. Removal of Demethyl and Didemethyl Impurites from a Crude Citalopram Mixture Methylisocyanate polystyrene resin (0.34 g, 0.18 mol isocyanate) is added to a solution of 5-CN (0.92 g) in Toluene (10 g) and stirred at room temperature.

After 2 h at room temperature, the resin was filtered and Toluene was evaporated in vacuo (50–60° C. at 5–10 mm Hg) to afford product with 70% less demethyl impurity (A).

L. SMB Purification of Citalopram-HBr

Experimental

The feed mixture is an oil recovered from the cyanation step and contains several impurities (polar and non-polar). These impurities can mostly be removed by standard reworking of the product (e.g., by crystallization and solvent exchange). However, one impurity is not removed by these techniques. This impurity is the starting material of the previous step. It is the 5-Br intermediate that is converted into Citalopram during the cyanation step.

Figure 3:
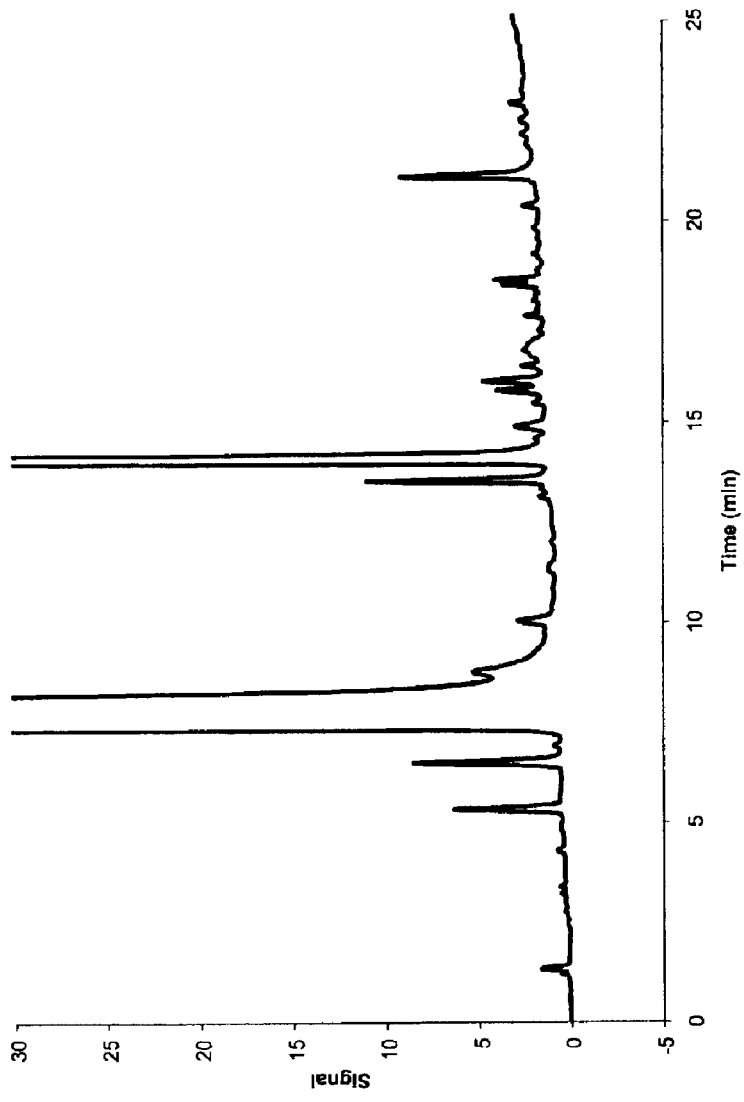
FIG. 3 illustrates an example of a feed composition to be purified.

The separation of a mixture of Citalopram and 5-Br intermediate in the proportion 95/5 (HPLC area % at 232-nm) was examined by chromatography and more specifically by the simulated moving bed technique. FIG. 3 (reverse phase analysis) gives an example of the feed composition. The largest peak is the Citalopram peak. The second largest peak is the 5-Br intermediate. The other peaks are of lesser interest for the chromatographic separation.

The following equipment was used for the experiment. SMB unit: Licosep laboratory unit from NOVASEP (Brabois (54), France) equipped with 8 axial compression columns from MERCK (Darmstadt, Germany). Each column was 50-mm internal diameter and was prepared using 110-g of CHIRALCEL OD™ 20-μm chiral stationary phase (Chiral Technologies Inc, Exton, USA). The average column length was 10.3-cm. The mobile phase used for the separation was a mixture of ethanol (denatured with n-heptane) and n-heptane in the proportion 10/90% (v/v.). Triethylamine was added as a modifier (0.2% total volume). The separation was conducted at 30° C. Under such conditions, the compound of interest (Citalopram) is the second eluting compound and will be designed as the Extract, 5-Br will be the Raffinate.

Each column was individually tested with a diluted solution of the mixture to be separated (14.2-g/l). The injected volume was 0.5-ml. Detection was performed at 254-nm and the flow rate was 100-ml/min. The 5-Br average elution time is 1.92-min while the Citalopram has an averaged elution time of 3.10-min. The average $t_0$ (or dead volume) of the column was 1.51-min. The average retention factor for the 5-Br was 0.27 and was 1.04 for the Citalopram. The average selectivity of the separation was 3.84.

Separation Parameters

The separation was conducted using 703.1 g of a mixture of Citalopram and 5-Br prepared according to the cyanation procedure. The feed composition is 95% of Citalopram and 5% of 5-Br (area % by HPLC at 232-nm). The feed contains other impurities, but they were not taken into account in the calculation of the feed composition. The feed concentration for this step was 22.7-g/l.

The set of parameters used for the separation was:

Product Recovery

Each recovered fraction (extract and raffinate) was evaporated in 20-L rotary evaporators (Genser, Germany). The Extract fraction was evaporated to dryness and the product was recovered as a crystal. The evaporation step was conducted at 40-° C. (waster bath) and under vacuum (150-mbar to start the process and down to 80-mbar for drying the product) with 50-rpm for the flask speed.

The solvent recovered was sampled and tested and acceptable low amount of product was detected (traces).

The raffinate was re-dissolved in a small amount of ethanol denatured and evaporated in a 1-L flask using the laboratory evaporator (Buchii). The raffinate product (5-Br) was recovered as a viscous oil.

A sample of each recovered fraction was analyzed using a $C_{18}$ column (reverse phase) and a gradient of water with TFA (trifluoroaceticacid) and acetonitrile with TFA.

Separation Performance

The total quantity of product recovered is 675.3-g (all fractions included), which gives an overall yield for the process of 96%. The 4% loss is due to product loss in the equipment (tanks walls, tubing, SMB unit) and when recovering the fractions.

The expected quantity of 5-CN to be recovered was 641.5-g. The total extract collected was 576.2-g representing a recovery yield of 89.8%.

Figure 4:
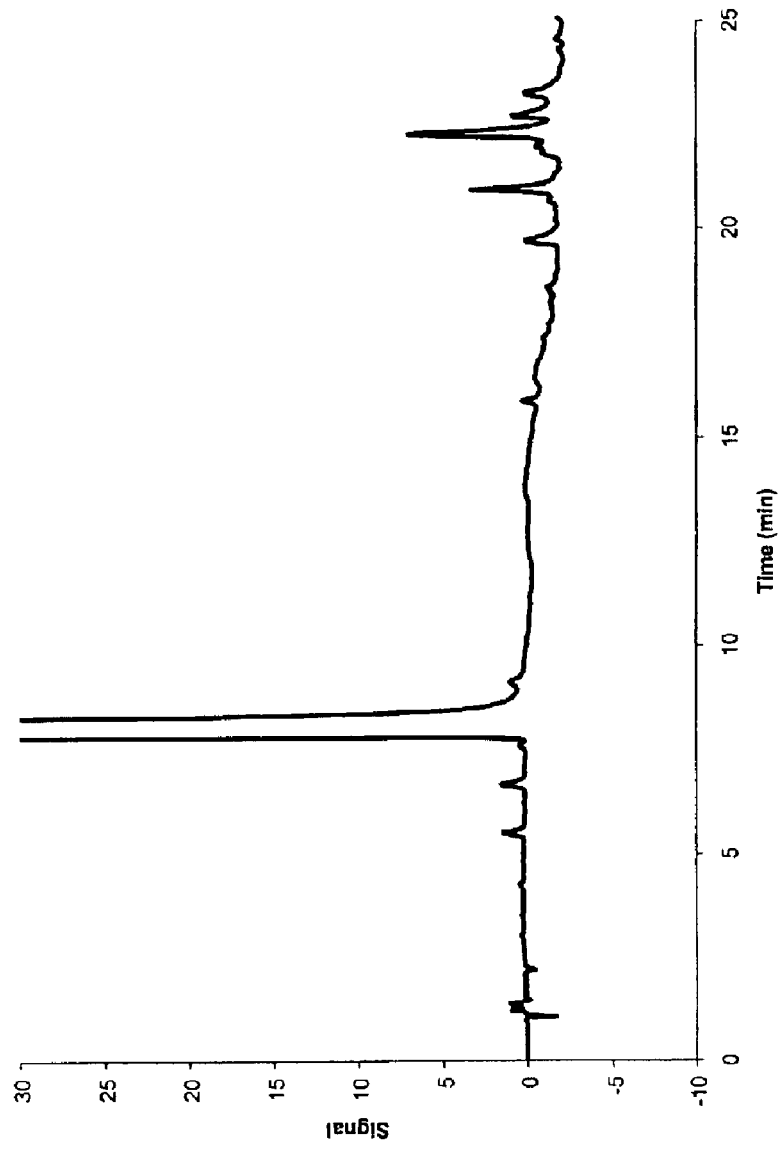
FIG. 4 illustrates that the product contained in the extract, i.e., the recovered extract, does not contain any detectable amounts of 5-Br.
Figure 5:
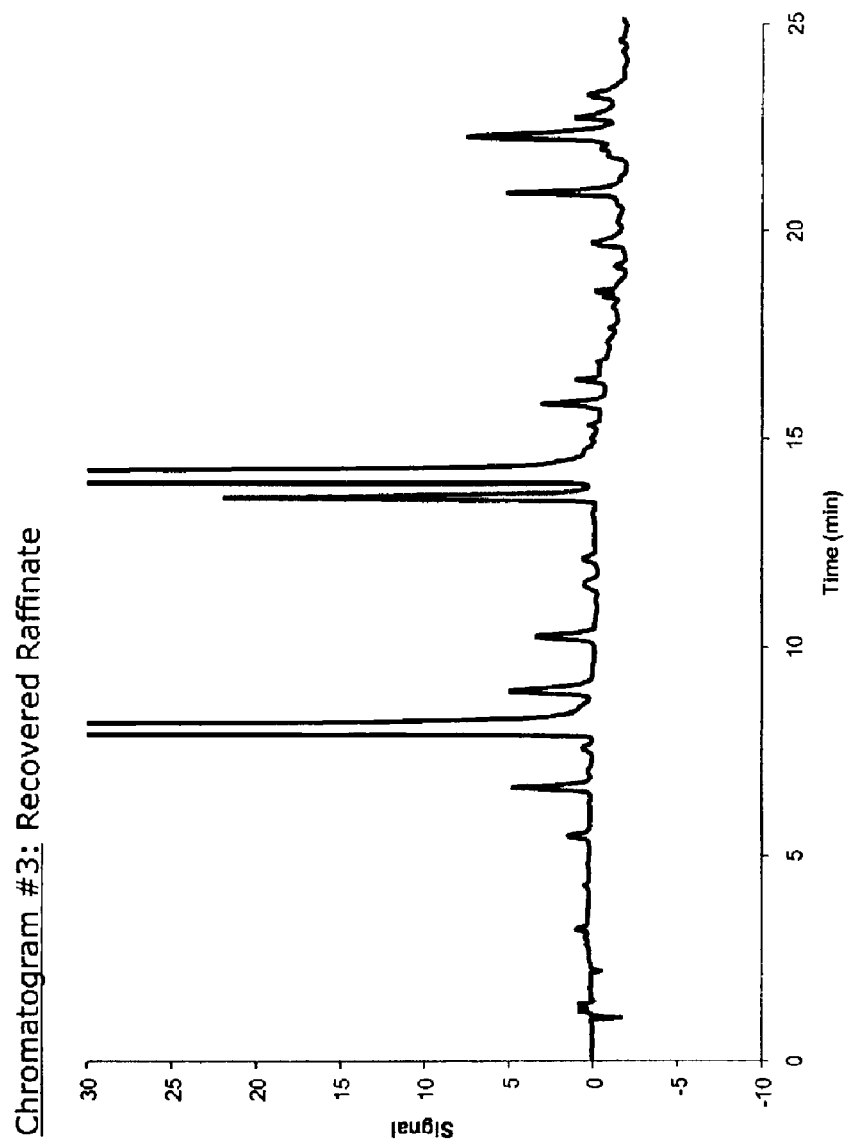
FIG. 5 illustrates the recovered raffinate.

The product obtained in the extract does not contain detectable amount of 5-Br (see, FIGS. 4 and 5).

Based on these experimental data, the production rate for the separation is 1.31-kg/d of 5-CN at 17 bars. This corresponds to a productivity of 1.49 kg of Citalopram per day per kg of CSP at 17 bars (free of 5-Br).

[Let's discuss whether or not to include the loading study as well as the other information in the discussion section]

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A method for preparing a salt of the compound of Formula III having the following structure:

| Period min | Eluent ml/min | Zone I (recycle) ml/min | Extract ml/min | Zone II ml/min | Feed ml/min | Zone III ml/min | Raffinate ml/min | Zone IV ml/min |
|---|---|---|---|---|---|---|---|---|
| 1.65 | 86.7 | 190 | 76.7 | 113.3 | 40 @ 22.7 g/l | 153.3 | 50 | 103.3 |

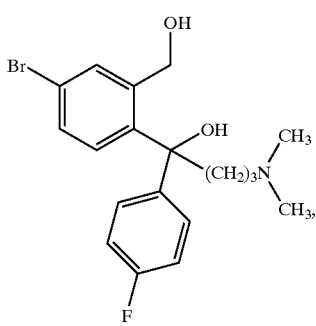

said method comprising:

(a) contacting a compound of Formula I having the following structure:

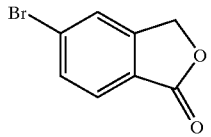

with 4-fluorophenyl magnesium bromide to form an intermediate of Formula II having the following structure:

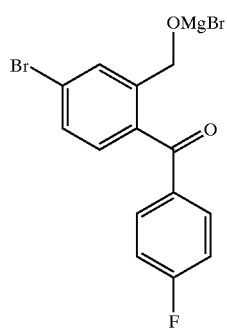

(b) contacting said intermediate of Formula II with dimethylaminopropyl magnesium chloride in an organic solvent to form a reaction mixture; and (c) quenching said reaction mixture with an acid to form a product mixture comprising said salt of the compound of Formula III.

2. The method of claim 1, wherein said salt of the compound of Formula II is an acid salt.

3. The method of claim 2, wherein said acid salt is a member selected from the group consisting of a HCl salt, a HBr salt, a $H_2SO_4$ salt, a $H_3PO_4$ salt, a methanesulfonic acid salt, a trifluoroacetic acid salt, an acetic acid salt, a fumaric acid salt and a citric acid salt.

4. The method of claim 1, wherein said organic solvent in step (b) is a member selected from the group consisting of diethylether, t-butylmethylether, THF, dioxane, toluene, xylene and mixtures thereof.

5. The method of claim 1, wherein said organic solvent in step (b) is a mixture of THF and toluene.

6. The method of claim 1, wherein said acid in step (c) is a member selected from the group consisting of HCl, HBr, $H_2SO_4$, $H_3PO_4$, methanesulfonic acid, trifluoroacetic acid, acetic acid, fumaric acid and citric acid.

7. The method of claim 1, wherein said acid is aqueous HCl.

8. The method of claim 1 further comprising:
(d) isolating said salt of the compound of Formula III from said product mixture.

9. The method of claim 8, wherein step (d) comprises:
(i) filtering said product mixture to obtain said salt of the compound of Formula III.

10. The method of claim 9, wherein step (d) further comprises:
(ii) washing said salt of the compound of Fonnula III with water and toluene.

11. The method of claim 10, wherein step (d) further comprises:
(iii) recrystallizing said salt of the compound of Formula III from a member selected from the group consisting of 1-butanol, 2-butanol and water.

12. The method of claim 11, wherein step (d) further comprises:
(iv) recrystallizing said salt of the compound of Formula III from 2-butanol.

* * * * *

UNITED STATES PATENT AND TRADEMARK OFFICE
CERTIFICATE OF CORRECTION

PATENT NO. : 6,967,259 B2  
DATED : November 22, 2005  
INVENTOR(S) : Aslam A. Malik et al.

It is certified that error appears in the above-identified patent and that said Letters Patent is hereby corrected as shown below:

<u>Column 18,</u>  
Lines 43-44, delete in their entirety.

Signed and Sealed this

Sixteenth Day of May, 2006

JON W. DUDAS  
*Director of the United States Patent and Trademark Office*